United States Patent [19]  [11] 4,089,863
Darragh  [45] May 16, 1978

[54] PROCESS FOR PRODUCING PYRIDINE AND METHYL PYRIDINES

[75] Inventor: John Irvine Darragh, Runcorn, England

[73] Assignee: Imperial Chemical Industries Limited, London, England

[21] Appl. No.: 712,377

[22] Filed: Aug. 6, 1976

[30] Foreign Application Priority Data

Aug. 22, 1975 United Kingdom ............... 34971/75

[51] Int. Cl.$^2$ .......................................... C07D 213/10
[52] U.S. Cl. ................................................. 260/290 P
[58] Field of Search ..................................... 260/290 P

[56] References Cited

U.S. PATENT DOCUMENTS

3,381,011 4/1968 Hall .................................. 260/290 P

Primary Examiner—Alan L. Rotman
Attorney, Agent, or Firm—Cushman, Darby & Cushman

[57] ABSTRACT

Formaldehyde, acetaldehyde and ammonia are reacted in the vapor phase over a catalyst in the substantial absence of molecular oxygen and in the presence of at least three moles of steam for each mole of total aldehyde reactants. The useful life of the catalyst in the production of pyridine and/or methyl pyridines by this reaction is thereby increased and the coking of the catalyst is reduced.

8 Claims, No Drawings

PROCESS FOR PRODUCING PYRIDINE AND METHYL PYRIDINES

This invention relates to the manufacture of organic bases and more particularly to the manufacture of pyridine and methylpyridines.

It has long been known that pyridine and methylpyridines may be produced by the interaction of formaldehyde, acetaldehyde and ammonia in the vapour phase in the presence of a catalyst; such a process is described, for example, in the specification of U.K. Pat. No. 742,643

In the specification of U.K. Pat. No. 1,070,664 there is described a process wherein oxygen (and optionally steam) is included in the reaction mixture comprising formaldehyde, acetaldehyde and ammonia; it is stated that the inclusion of oxygen enhances the yield of pyridine and results in the production of only small amounts of the picolines (methylpyridines). It is stated that the molar ratio of total organic reactants to oxygen may vary widely, for example from 10:1 to 1:10 but is preferably within the range from 6:1 to 1:5 (i.e. from 0.17 to 5 moles of oxygen per mole of total organic reactants).

In the specification of U.K. Pat. No. 1,235,390 there is described a process for the production of pyridine and beta-picoline by reaction of formaldehyde, acetaldehyde and ammonia in the vapour phase at elevated temperature over certain fluidised catalysts and in the absence of added oxygen. It is stated therein that a most convenient way of feeding formaldehyde (to the process) is to dissolve the formaldehyde in a suitable solvent, e.g. an alcohol, preferably methanol, or water. It is stated that while it is desirable to keep the amount of solvent used to a minimum the vaporised solvent may also be passed through the reactor. The specification of U.K. Pat. No. 1,235,390 contains no general teaching about the proportion of water (or steam) to be employed but each of the seven Examples therein shows the use of 0.26 mole $H_2O$ and 1.70 moles of formaldehyde plus acetaldehyde (i.e. 0.15 mole steam for each mole of total aldehyde reactants.)

We have now found that the reaction between formaldehyde, acetaldehyde and ammonia may advantageously be carried out in the absence of molecular oxygen (or in the presence of not more than 0.05 mole of molecular oxygen for each mole of total aldehyde reactants) provided that the proportion of steam in the reaction mixture is at least 3 moles of steam for each mole of total aldehyde reactants. Under these conditions the deposition of carbonaceous materials upon the catalyst is considerably reduced and the useful life of the catalyst is consequently extended. Another advantage of carrying out the reaction in the absence of oxygen (or in the presence of the defined relatively small proportion of oxygen) is that the hazard of explosion is considerably reduced.

Thus according to the present invention there is provided a process for the manufacture of pyridine and/or methylpyridines which comprises the catalytic vapour-phase reaction of formaldehyde, acetaldehyde and ammonia in the absence of molecular oxygen (or in the presence of not more than 0.05 mole of molecular oxygen for each mole of total aldehyde reactants) and in the presence of at least 3 moles of steam for each mole of total aldehyde reactants.

While it is preferred to carry out the reaction in the absence of molecular oxygen, it will be understood that rigorous precautions need not be taken to exclude molecular oxygen from the system since the defined relatively low proportions of oxygen (i.e. not more than 0.05 mole of molecular oxygen for each mole of total aldehyde reactants) may be tolerated as not markedly reducing the effective life of the catalyst.

It is known in the art that a wide variety of catalysts may be employed in the catalytic vapour-phase reaction between formaldehyde, acetaldehyde and ammonia. Suitable catalysts for use in the process of the present invention include, for example, those mentioned in the specifications already referred to herein. The preferred catalysts are those comprising alumina (especially silica-alumina).

The catalyst may be employed either as a fixed bed or in the form of a fluidised bed.

The reaction may be carried out over a wide range of temperature, for example from 300° to 550° C but the preferred temperatures are those in the range 350° to 500° C.

The reaction is preferably carried out at substantially atmospheric pressure but higher or lower pressures may be used.

The molar ratio of ammonia to total aldehyde reactants is preferably at least 0.5 to 1. It is especially preferred to use at least 1 mole of ammonia per mole of total aldehyde reactants, for example from 1 to 5 moles of ammonia per mole of total aldehyde reactants.

The relative proportions of formaldehyde and acetaldehyde may vary widely but the reaction mixture preferably contains at least 0.2 mole of formaldehyde per mole of acetaldehyde (for example from 0.5 to 3 moles) of formaldehyde per mole of acetaldehyde).

The proportion of steam employed must, as already stated, be at least 3 moles of steam for each mole of total aldehyde reactants. While the proportion of steam may be considerably in excess of this ratio an upper limit will, in practice, be imposed by the desirability of maintaining an acceptably high throughout of the reactants. Thus while the proportion of steam may be, for example, from 3 to 20 moles of steam per mole of total aldehyde reactants there is in general little to be gained by using more than about 10 moles of steam per mole of total aldehyde reactants.

Formaldehyde and acetaldehyde may be introduced as such or in the form of a compound giving rise thereto under reaction conditions. Thus, for example, ethanol may be used as a source of acetaldehyde while formaldehyde, trioxane, methanol or methylal may be used as sources of formaldehyde.

Pyridine and/or methylpyridines may be separated from the reaction products by known methods, for example by distillation, extraction or a combination of such methods.

When pyridine itself is the product mainly desired, the reaction products of the present invention may conveniently be passed directly to a dealkylation process without an intermediate separation stage. Thus the whole of the reaction products (including pyridine, methylpyridines and excess steam) may be maintained in the vapour phase and passed continuously to a stage wherein the methylpyridines are demethylated in the presence of a dealkylation catalyst, which may be the same as, or different from, the catalyst employed in the stage of the primary reaction between formaldehyde, acetaldehyde and ammonia.

If desired, further steam may be introduced at the demethylation stage (or between the primary stage and the demethylation stage). Molecular oxygen may also be introduced at the demethylation stage (or between the primary stage and the demethylation stage.)

The invention is illustrated by the following Examples in which all parts and percentages are by weight unless otherwise stated.

EXAMPLE 1

Formaldehyde, acetaldehyde and ammonia were reacted in the vapour phase at a temperature of 450° C over a fluidised catalyst in the absence of oxygen but in the presence of steam. The relative molar ratios fed to the fluidised catalyst per mole of formaldehyde were 2 moles of acetaldehyde; 10.8 moles of steam; 2.7 moles of ammonia and 8 moles of nitrogen.

The acetaldehyde and formaldehyde were passed as an aqueous solution to a vaporiser, and the vapours were passed to the fluidised catalyst; the remaining gases were supplied to the fluidised catalyst via rotameters. The catalyst was a silica/alumina cracking catalyst containing 13% alumina, commercially available as "Synclyst" (Trade Mark) - grade 3A MS13/HD from J Crosfield and Company Limited, Warrington. The contact time was 5 seconds.

The reaction was continued for 6 hours, the products being condensed and analysed to determine the efficiency of conversion to pyridine bases and the ratio of pyridine to picolines in the product. The reaction was terminated and a portion of the catalyst was analysed to determine the carbon content. The reaction was then re-started using the catalyst from the previous production and was continued for a further 6 hours, the efficiency of conversion being determined over this period as before.

The reaction was again terminated and the carbon content of the catalyst determined. The same catalyst was finally run for a further 4 hours and the same measurements were taken over this period. The results are presented in Table 1.

TABLE 1

| Catalyst Age (hours) | % Efficiency of Conversion to Pyridine Bases (based on Carbon Fed) | Molar Ratio Pyridine/ Picolines | % Carbon Content of Catalyst |
|---|---|---|---|
| 6 | 72.7 | 1.4 | 6.2 |
| 12 | 70.0 | 1.5 | 10.2 |
| 16 | 66.7 | 1.5 | 11.1 |

EXAMPLE 2

The procedure of Example 1 was repeated using a fresh catalyst but in the presence of 0.02 moles of oxygen per mole of total aldehyde reactants.

Thus the relative molar ratios fed to the fluidised catalyst per mole of formaldehyde were 2 moles of acetaldehyde; 10.8 moles of steam; 2.7 moles of ammonia; 0.29 moles of air (i.e. approximately 0.06 moles oxygen and 0.23 moles nitrogen); and 7.4 moles of additional nitrogen.

The results for the three successive periods of use of the catalyst are given in Table 2.

TABLE 2

| Catalyst Age (hours) | % Efficiency of Conversion to Pyridine Bases (based on Carbon Fed) | Molar Ratio Pyridine/ Picolines | % Carbon Content of Catalyst |
|---|---|---|---|
| 6 | 68.1 | 1.4 | 7.0 |
| 12 | 71.4 | 1.5 | 11.3 |
| 16 | 72.7 | 1.6 | 14.0 |

COMPARISON 1

By way of comparison, the procedure of Example 1, was repeated using a fresh catalyst but in the presence of 0.2 moles of oxygen per mole of total aldehyde reactants. The relative molar ratios fed to the fluidised catalyst per mole of formaldehyde were 2 moles of acetaldehyde; 10.8 moles of steam; 2.6 moles of ammonia; 2.8 moles of air (i.e. approximately 0.6 moles of oxygen and 2.7 moles nitrogen) and 2.5 moles of additional nitrogen.

The results for the three successive periods of use of the catalyst are given in Table 3.

TABLE 3

| Catalyst Age (hours) | % Efficiency of Conversion to Pyridine Bases (based on Carbon Fed) | Molar Ratio Pyridine/ Picolines | % Carbon Content of Catalyst |
|---|---|---|---|
| 6 | 74.0 | 2.8 | 12.1 |
| 12 | 59.1 | 2.7 | 17.1 |
| 16 | 47.7 | 3.3 | 22.9 |

It can be seen that, in the presence of more than 0.05 moles oxygen per mole of total aldehyde reactants, the efficiency of the reaction falls off rapidly as the catalyst ages, and the carbon content of the catalyst is considerably increased over that of Example 1.

COMPARISON 2

By way of further comparison, the procedure of Example 1 was repeated using a fresh catalyst but in the presence of 0.4 moles of oxygen per mole of total aldehyde reactants. The relative molar ratios fed to the fluidised catalyst per mole of formaldehyde were 2 moles acetaldehyde; 10.8 moles steam; 2.7 moles ammonia; 5.5 moles air (i.e. approximately 1.1 mole oxygen and 4.4 moles nitrogen); and 2.5 moles additional nitrogen.

The procedure of Example 1 was repeated and the corresponding results are presented in Table 4. It can be seen that, in the presence of more than 0.05 moles per mole of total aldehyde reactants, the efficiency of the reaction falls off rapidly as the catalyst ages, and the carbon content of the catalyst is considerably increased over that of Example 1.

TABLE 4

| Catalyst Age (hours) | % Efficiency of Conversion to Pyridine Bases (based on Carbon Fed) | Molar Ratio Pyridine/ Picolines | % Carbon Content of Catalyst |
|---|---|---|---|
| 6 | 69.2 | 5.9 | 15.1 |
| 12 | 49.8 | 7.9 | 23.6 |
| 16 | 28.4 | 6.4 | 28.7 |

I claim:

1. A process for the manufacture of pyridine and methyl pyridines which comprises the catalytic vapour-phase reaction at a temperature of from 300° to 550° C of formaldehyde, acetaldehyde and ammonia in the presence of not more than 0.05 moles of molecular oxygen for each mole of total aldehyde reactants and in the presence of a silica-alumina catalyst and at least 3 moles of steam for each mole of total aldehyde reactants, wherein the molar ratio of ammonia to total aldehyde reactants is at least 0.5 moles of ammonia per mole of total aldehyde reactants and the reaction mixture contains at least 0.2 moles of formaldehyde per mole of acetaldehyde.

2. A process according to claim 1 wherein the temperature is from 350° to 500° C.

3. A process according to claim 1 wherein the molar ratio of ammonia to total aldehyde reactants is from 1 to 5 moles of ammonia per mole of total aldehyde reactants.

4. A process according to claim 1 wherein the reaction mixture contains from 0.5 to 3 moles of formaldehyde per mole of acetaldehyde.

5. A process according to claim 1 wherein the proportion of steam is from 3 to 20 moles of steam per mole of total aldehyde reactants.

6. A process according to claim 5 wherein the proportion of steam is from 3 to 10 moles of steam per mole of total aldehyde reactants.

7. A process according to claim wherein the reaction is carried out in the presence of a silica/alumina catalyst.

8. A process according to claim 1 wherein said reaction is carried out in the absence of molecular oxygen.

* * * * *